United States Patent [19]

Lentz

[11] Patent Number: 4,654,031

[45] Date of Patent: Mar. 31, 1987

[54] FLASH CHAMBER

[75] Inventor: David J. Lentz, Salt Lake City, Utah

[73] Assignee: Warner-Lambert Company, Morris Plains, N.J.

[21] Appl. No.: 723,247

[22] Filed: Apr. 15, 1985

[51] Int. Cl.$^4$ .............................................. A61M 5/14
[52] U.S. Cl. ..................... 604/168; 604/272; 604/256; 128/763
[58] Field of Search ................ 604/272, 52, 161, 164, 604/165, 168, 192, 147, 240, 243, 245, 246, 256, 257, 263, 272, 409, 900, 169; 128/763, 766, 771; 206/364, 365, 438

[56] References Cited

U.S. PATENT DOCUMENTS

| 3,021,942 | 2/1962 | Hamilton | 604/243 |
| 3,030,954 | 4/1962 | Thornton, Jr. | 604/251 |
| 3,333,682 | 8/1967 | Burke | 604/272 |
| 3,352,306 | 11/1967 | Hirsch | 604/168 |
| 4,046,144 | 9/1977 | McFarlane | 604/168 |
| 4,108,175 | 8/1978 | Orton | 604/168 |
| 4,191,183 | 5/1980 | Mendelson | 604/80 |
| 4,269,186 | 5/1981 | Loveless et al. | 604/168 |
| 4,307,731 | 12/1981 | Kaufman | 128/766 |
| 4,365,630 | 12/1982 | McFarlane | 604/168 |
| 4,440,207 | 4/1984 | Genatempo et al. | 604/256 |
| 4,589,421 | 5/1986 | Ullman | 128/763 |

FOREIGN PATENT DOCUMENTS

| 0139872 | 5/1985 | European Pat. Off. | 604/168 |
| 83/00281 | 2/1983 | PCT Int'l Appl. | 128/763 |

Primary Examiner—Stephen C. Pellegrino
Attorney, Agent, or Firm—Aaron Passman

[57] ABSTRACT

A flash chamber formed of two molded components being a cap which fits over a hollow hub and conjugates therewith to form a tortuous path through the hub and then between the outside of the hub and the inside of the cap.

9 Claims, 3 Drawing Figures

FLASH CHAMBER

BACKGROUND OF THE INVENTION

This invention relates to flash chambers and more particularly the venting of flash chambers. The flash chamber is the portion of a catheter unit which is held by the medical technician during the insertion (by puncture of the needle carrying the catheter coaxially thereabout) into the lumen of a blood vessel. Once puncture has been made by penetration with the tip of the hollow needle, blood spurts up through the needle and appears to flash into a chamber affixed at the end near the medic (not the patient) of the hollow needle. A tourniquet is used to facilitate the location of the vein and increase local blood pressure thereby causing the spurt. The medical technician knows of successful puncture or penetration into the vein because of the flash into the chamber.

Flash chambers are usually vented by means of an opening at the end remote from where the hollow needle is connected. This opening is covered by a filter in the form of a porous membrane usually of spun bonded polyolefinic material which is lint free and is affixed or held across the opening at the end of the flash chamber that the medic holds. Some flash chambers use a circuitous path to control flow of flashed blood from the needle end of the flash chamber to the end most proximate the medic but still have a filter element. The flash chamber concept is to allow the medic to see when the puncture is successful and yet prevent the spillage of blood during time required for the insertion procedure. Various approaches to making the path in the flash chamber circuitous have been tried, which rely on a change of direction of flow normal to the axis of the needle at least once or several times during the process of venting. The ultimate disposition of the flash blood is at the end of the flash chamber closest to the medical technician.

With the current concern about blood transmitted diseases such as tuberculosis, hepatitis, AIDS, and the like, the fear is that disease will be transmitted if the medical technician contacts the patient's blood. Similarly, the medical technicians are exposed to various other patients and equipment with a variety of infection, contagious diseases, bacteria and/or virus about the hospital whereby flashed blood might pick up same and reach the patient. The problem is to prevent the blood from leaking from the flash chamber near the surfaces where medics normally handle the catheter. These problems have caused concern about the way in which the flashed blood is vented.

OBJECTS OF THE DISCLOSURE

It is consistent with the objects of the disclosure to provide a flash chamber which is vented in a manner whereby the blood is either inhibited from leaving the flash chamber or in the event same leaves the flash chamber, the exit point is located closer to the patient and further from the medical technician.

Another object of the invention is to provide a flash chamber with a tortuous path which permits adequate venting while at the same time restricts the out flow of flashed blood.

It is a further object of the present disclosure to teach means by which the flash chamber may be fashioned into an integral container unit which is shaped for easy handling of the needle and its catheter with secure confinement of and proper venting of the flashed blood.

SUMMARY OF THE DISCLOSURE

Disclosed is a flash chamber for use in connection with an over the needle catheter and adapter set wherein the flash chamber consists of two primary components. A cap, being a hollow elongated tubular compartment opened at one end and closed at the other, into which a needle carrying hub is snap-fit to provide a tortuous path therebetween. Flashed blood is confined yet vented after successful penetration of the blood vessel lumen but prior to removal of the needle and subsequent connection of the administration set to the adapter and placed catheter.

The relationship between the cap and the hub is such that the flow of blood fluid is through the hollow hub into the closed end of the cap where the fluid must change direction and thereafter flow by means of another path toward the direction from which it came but apart from the original flow path to a venting exit positioned close to the needle end of the hub, i.e. the open end of the cap.

In operation, the medic grasps the outside of the cap near its closed end and since the flow and venting of blood is toward the open end of the cap away from the medic, contamination by or infection transmission to the medic is prevented. The ultimate vent opening of the cap and hub combination is defined by a pair of faces on each forming a radially extending closely spaced gap. The faces are sufficiently flat and tightly held together to inhibit flow of blood but permit the flow of gases during venting. The establishment of the relationship of these faces is controlled by the snap-fit interengagement between the cap and hub. That is to say that, the relative axial positions of the snap engaging components can be used to assure the end gap relationship between the respective faces on the cap and hub.

DETAILED DESCRIPTION OF THE DISCLOSURE

Figure 1:
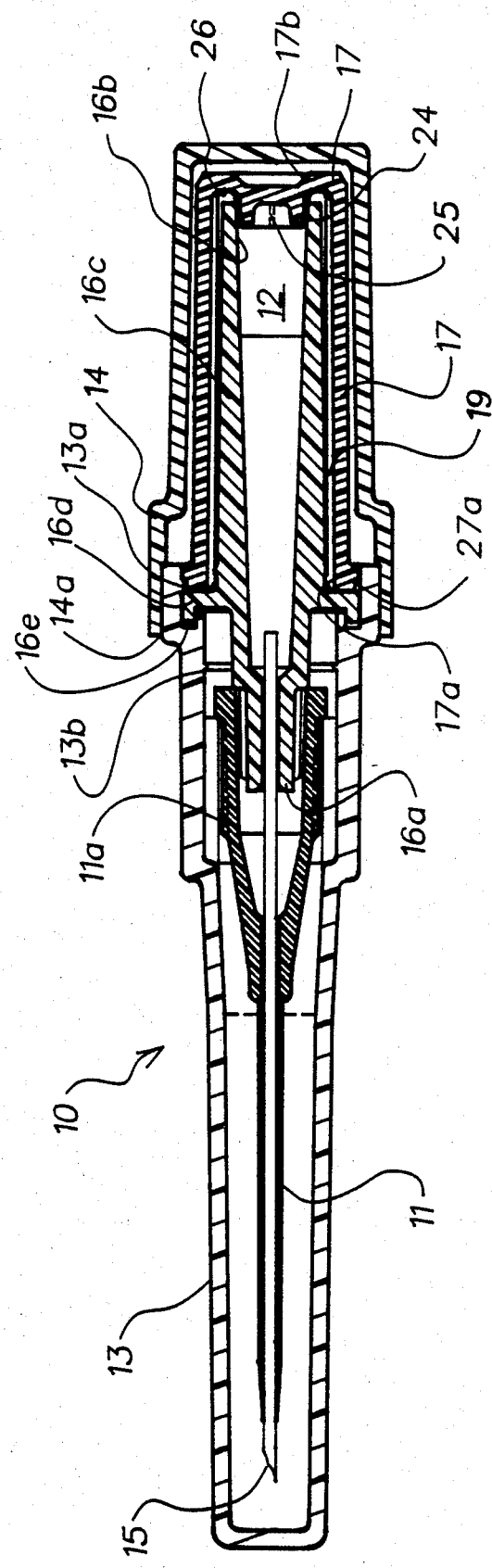
FIG. 1 is a side cross sectional view of the hub and cap with their respective adapter and catheter needle and over package.

In FIG. 1 is shown a complete package 10 for a catheter 11, flash chamber 12, needle guard 13, and chamber cover 14. The needle 15 is held in fluid communication with hub 16 of the flash chamber 12. All of the various components are molded of polymeric substance except the needle which is a thin wall hollow tubular steel unit sharpened at the patient end. In use, the needle guard 13 and the flash chamber cover 14 are removed whereupon the medic may insert the needle 15 into a patient to puncture a blood vessel. Once penetration and puncture have been complete, blood will course through the hollow needle up into the flash chamber 12 located in the hollow central portion of the hub 16. More specifically, hub 16, FIG. 1, is an elongated tubular molded component which receives the needle 15 at one end and holds same for fluid communication. In particular, hub 16 has a needle end 16a which is hollow, elongated and includes an inner bore designed to surround the end of the needle and to therewith form a fluid coupling. At the end opposite 16a of hub 16 is an open portion 16b which tapers inwardly therefrom toward end 16a in order to facilitate molding the deep elongated hollow which comprises the flash chamber 12. Between ends 16a and 16b is the body, 16c of the hub 16 about which and located toward the end 16a is a radially extending shoulder 16d. The axial location of shoulder 16d is by design positioned toward the end 16a.

In FIG. 1 surrounding the hub 16 is a cap 17 being a hollow tubular elongated component opened at one end with a mouth 17a and closed at the other with a bottom 17b. The inner well formed within the cap 17 is designed to receive the body 16c of the hub 16. The inner well of the cap 17 has an elongated axial length at least as great as the distance from the hub open portion 16b to the extending radial shoulder 16d.

The hub 16 nests within the inner well of the cap 17. The assembled axial relationship between cap 17 and hub 16 is defined by an axial holding means 18 shown in enlarged detail in FIG. 2. The cap 17 is an enlarged partial cross section and the hub 16 is an enlarged partial full view. In particular, the cap 17 includes internal longitudinal ribs 19 which terminate near mouth 17a in an inwardly extending nib 19a, see FIGS. 1, 2 and 3.

Figure 2:
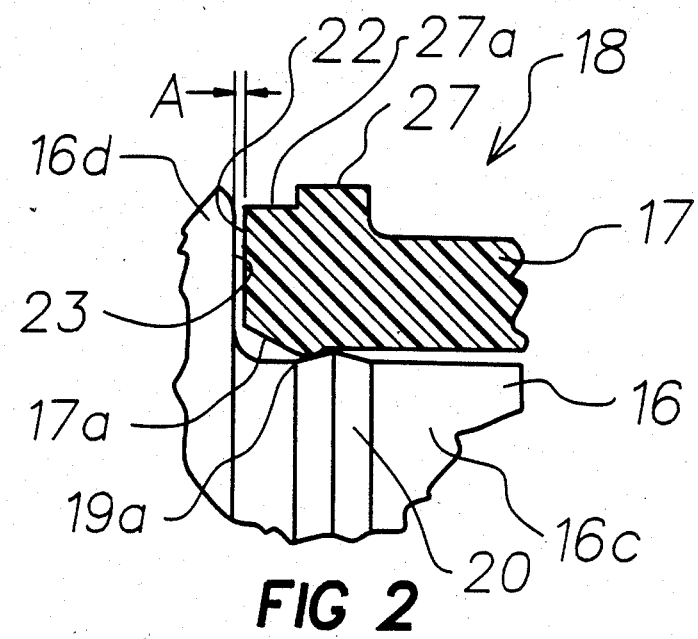
FIG. 2 is an enlarged view of the portions of the cap and hub wherein the snap-fit is provided.

In FIG. 2, the nib 19a cooperates with an annular bump 20 which circumscribes the body 16c of the hub 16. The axial position of bump 20 is closer to end 16a of hub 16. Between each of the longitudinal ribs 19 is a longitudinal recess 21 which extends along the inside wall of cap 17 from the mouth 17a to the bottom 17b. Blood received in flash chamber 12 may flow along the recesses 21 between the bottom 17b and the mouth 17a. The recesses 21 form longitudinal channel like passageways between the outside of the hub body 16c and the inside of the cap 17. The difference in curvature of the outside of cap 17 and the inside of recess 21 acts as a lens to magnify the flashed blood.

As best seen in FIG. 2, there is a gap "A" between the cap end face 22 and the shoulder face 23 the latter being the face portion of the radially extending shoulder 16d. Gap "A" can be any spacing desired and is defined by the relationship between the nib 19a and the annular bump 20. That is to say that, the relative positions of the nib 19a to the face 22 will define how tightly the cap 17 fits against the shoulder 16d and how small the gap "A" is as a consequence of that fit. In practice, the fit that has been found to work is a practically flush fit relying only on the clearances which are formed as a result of imperfections in the molds. This provides a minimal gap which easily passes blood gases but inhibits the flow of liquid blood. Blood which passes through needle 15 into the flash chamber 12 is then redirected up and then along recesses 21 toward the needle end of the flash chamber. The flashed blood must pass between gap "A" before it can reach the outside.

Figure 3:
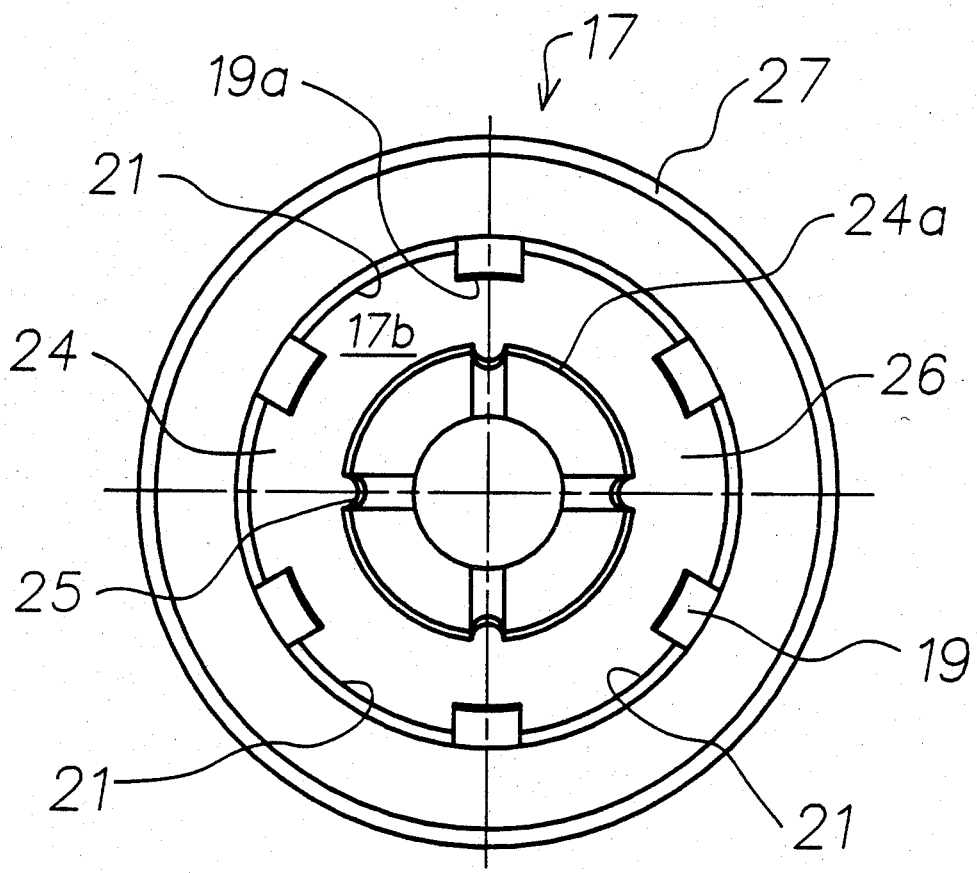
FIG. 3 is an end view of just the cap as would be seen if examined looking into the open end.

At the bottom 17b of the cap 17 see FIGS. 1 and 3, there is molded an upstanding annular ring 24 which is centered in the bottom 17b of the cap 17. The ring 24 includes a series of peripheral grooves 25 which extend axially upward from bottom 17b along the outer surface 24a of the ring 24. Each groove 25 is provided to encourage blood flow from chamber 12 through the grooves 25 into the bottom 17b of the cap and more specifically, into a well 26 defined by the annular space between the annular ring 24 and the inside bottom of the cap 17. It is well 26 which turns the direction of blood flow back toward the needle end 16a of the hub 16. As pointed out the blood flows along the recesses 21 axially toward the needle end 16a of the hub 16 toward the gap "A". The outer surface 24a is sized to fit neatly within the open end portion 16b of the hub 16 but because of the grooves 25 provided about the outer surface 24a of the annular ring 24 blood can flow. It can be appreciated that the axial positioning of the cap 17 relative to the hub 16 is such that at one end 16b it is centered by the annular ring 24 and at the other end it is captured and located by the interengagement of the bump 20 and the nibs 19a.

FIG. 3 is a end view looking inwardly from the mouth 17a of the cap toward the bottom 17b. This view is shown as if no hub 16 were placed therein in order to fully illustrate the features on the inside of the cap 17. There is a peripheral lip 27 about the outer circumference of the cap 17, FIGS. 2 and 3. Lip 27 forms a recessed outer rim 27a circumscribing the mouth 17a of the cap 17. As best shown in FIGS. 1 and 2, when cap 17 is axially positioned on hub 16 whereby nib 19a and bump 20 are engaged and the predetermined axial positional relationship between these two components established, a space or peripheral annular groove is defined by the recessed outer rim 27a. It is that groove which is designed to receive the needle guard 13 and more particularly to conjugate with an inwardly annular catch 13a, FIG. 1, on the inside of the needle guard 13 where same is open to receive the combination of catheter 11 and its flash chamber 12. About the needle guard opening but radially inward therefrom is a shallow axially extending recess designed to cooperate with a similar axially outwardly extending part 16e on shoulder 16d whereby the needle guard 13 not only surrounds the flash chamber 12 i.e. the cap 17 and hub 16, but also acts to maintain the assembled relationship therebetween during shipping and prior to use.

The components for the flash chamber 12 are molded of polymeric substance, preferably transparent materials in order that the blood spurting through the needle 15 and flashing into the chamber 12 can be easily viewed during use i.e. after the insertion of the catheter into the lumen of the blood vessel. Once the flashed blood passes bottom 17b and starts to flow through the recesses 21 the magnifying effect of the aforementioned lens becomes readily apparent. For the cap 17, the preferred polymeric substance is K Resin by Phillips Petroleum and for the hub 16 the preferred material is PETG by Eastman Kodak. It should be appreciated that the hub 16 may be molded of an opaque material as the flashed blood could still be seen after it has passed through the hub 16 and made the turn at the bottom 17b of the cap 17 upon filling the recesses 21 in cap 17. The appropriate coloring of the hub 16 could be light enough such that the blood flowing in the space between the hub and cap would be readily visible. The surface of the preferred clear plastic components are highly polished to give the chamber 12 a jewel-like appearance.

The portion of the hub 16 and more specifically, the needle end 16a includes the part surrounding the needle 15. Upstanding axially positioned thereabout are ridges designed to center, locate and provide a slight interference fit with the inside open end of the adapter for catheter 11. And more particularly, the adapter portion 11a (an enlarged funnel like end on the catheter 11) is provided to except the tubing from an administration set (not shown) once the catheter has been placed and the needle and flash chamber removed. On the inside of the needle guard 13 is molded an inwardly disposed pull off ring 13b to help remove the molded needle guard from its mold during manufacture. This ring 13b has no function after the manufacturing process is complete.

The flash chamber cover 14, see FIG. 1, is a hollow cup like structure designed to fit over the flash chamber and over the outer radial peripheral portion of the cover guard where same snaps over the combination of hub 16 and cap 17. There is provided an inner annular recessed area 14a about the internal circumferential surface of the mouth of the flash chamber cover which recessed area 14a has an axial depth sufficient to receive a major portion of the open end of the needle guard 13. The flash chamber cover 14 is provided merely as an outer package or sealing portion for the unit whereby the consumer will see that the entire internal or working portion of the package 10 is protected from the standpoint of sterility. Were cover 14 missing. the needle guard 13 as provided and snapped into the recess 27a will seal the end gap "A" such that a sterilized unit without the cover 14 will be equally complete and useful.

While a particular configuration has been shown and described, the claims which follow discuss the concept more broadly than the particular embodiment disclosed and it is therefore the claims which should be read to clearly and fully understand the scope of the invention.

What is claimed is:

1. A flash chamber designed for carrying a hollow tubular needle for making the puncture site, carrying coaxially therewith a catheter into a human blood vessel and receiving the spurt of blood which passes through the needle and into the flashback chamber, comprising;
    a needle hub being a hollow tubular structure opened at both ends and so configured to hold the needle at one open end thereof in fluid communication permitting flow of fluid therethrough to the other end of said hub;
    a cap being a hollow elongated tubular component open at one end and closed at its other and along the inside of said cap recesses defined by spaced longitudinal ribs forming longitudinal channel-like passages between the outside of said hub structure and the inside of said cap and said cap being sized to fit over said other end of said needle hub and extend therefrom so that the open end of said cap interengages with the outer surface of said needle hub near its end most distal and is held thereto by conjugation therewith; and
    axial holding means positioned on said needle hub and designed for cooperative engagement with said cap ribs to provide a predetermined position of interengagement therebetween and for forming a tortuous path first through said hollow hub and then between said hub and said cap toward the needle end of said hub to inhibit the fluid flow therethrough and transversely over said axial holding means.

2. The flash chamber of claim 1 wherein said needle hub includes a radially extending shoulder near said one end having a face thereon exposed toward the closed end of said cap when hub and cap are assembled and said cap having a radially extending flange with a face positioned to form a parallel end gap between said faces of said hub and cap when same are assembled in conjugating interengagement in said predetermined axial position.

3. The flash chamber of claim 2 wherein said axially holding means includes an annular bump for conjugating interengagement with said ribs on said cap and said bump circumscribes said hollow tubular hub structure being axially positioned on the side of said radially extending hub shoulder closer to said face thereof and spaced away from said other end opening.

4. The flash chamber of claim 2 wherein said radially extending shoulder is positioned about said needle hub close to the needle end of said hub and said hub includes a tubular extending hollow portion therefrom designed to hold in fluid communication the proximal end of a needle and support thereabout on its outer peripheral surface an adapter and its catheter.

5. The flask chamber of claim 1 wherein said closed end of said hollow elongated tubular cap includes an upstanding annular ring centered therein and sized to fit within said needle hub other open end for centrally positioning same for allowing some flow therebetween.

6. The flash chamber of claim 5 wherein said annular ring has axially disposed grooves positioned to permit flow between said ring and said other open end of said needle hub.

7. The flash chamber of claim 6 wherein said cap about the open end thereof includes an inwardly extending nib on each of said ribs designed to interengage and conjugate with said annular bump on said needle hub.

8. The flash chamber of claim 5 wherein said hollow elongated tubular cap being made of a transparent polymer includes a lens defined by the difference in curvature of the outside of said cap and the inside tubular recess surface between said axially extending longitudinal ribs whereby blood flow within said recess in the area between said needle hub and said inside tubular wall of said cap is readily apparent.

9. A flash chamber for a needle and catheter combination comprising;
    a first member generally tubular and having at one end an inside opening for receiving a needle and said opening extending to an internal surface forming a first chamber open outwardly thereof at the other end of said first member, and
    a second member fashioned from a transparent material to fit over and enclose the end of said first member opposite said needle extending thereover and thereabout to interengage with the outer surface of said first member near the area of said needle to define a second chamber between the outside surface of said first member and the inside surface of said second member to provide a tortuous path through said first and second chambers said second member including a lens defined by the difference in curvature of the outside of said cap and the inside tubular surface.

* * * * *